US006059752A

United States Patent [19]
Segal

[11] Patent Number: 6,059,752

[45] **Date of Patent: *May 9, 2000**

[54] MECHANICAL APPARATUS AND METHOD FOR DILATING AND IRRADIATING A SITE OF TREATMENT

[76] Inventor: Jerome Segal, 6132 Western Ave., Chevy Chase, Md. 20815

[ * ] Notice: This patent is subject to a terminal disclaimer.

[21] Appl. No.: 08/969,220

[22] Filed: Nov. 13, 1997

Related U.S. Application Data

[63] Continuation-in-part of application No. 08/647,696, May 15, 1996, Pat. No. 5,755,708, which is a continuation-in-part of application No. 08/569,579, Dec. 8, 1995, Pat. No. 5,695,469, which is a continuation-in-part of application No. 08/353,558, Dec. 9, 1994, Pat. No. 5,527,282.

[51] Int. Cl.[7] .......... A61M 29/00

[52] U.S. Cl. .......... 604/107; 604/104; 606/194

[58] Field of Search .......... 604/104, 202, 604/53, 107, 106, 19; 606/194; 600/1, 3

[56] References Cited

U.S. PATENT DOCUMENTS

| | | | |
|---|---|---|---|
| 4,572,106 | 2/1986 | Gould et al. | 604/105 X |
| 5,484,304 | 1/1996 | Fearnot | 600/3 |
| 5,540,659 | 7/1996 | Teirstein | 604/104 |
| 5,683,345 | 11/1997 | Waksman et al. | 600/3 |
| 5,722,984 | 3/1998 | Fischell et al. | 606/198 |
| 5,730,698 | 3/1998 | Fischell et al. | 600/3 |
| 5,851,171 | 12/1998 | Gasson | 600/3 |

*Primary Examiner*—John G. Weiss
*Attorney, Agent, or Firm*—Michael E. Klicpera

[57] ABSTRACT

A mechanical dilatation and irradiation device for enlarging a flow passage of a vessel by dilating and irradiating an obstruction in the vessel. The present invention comprises a substantially cylindrically shaped expansion member and includes a means engaged to the expansion member for altering the distance between the proximal end and the distal end of the expansion member thereby transforming the expansion member between a diametrically contracted configuration to diametrically expanded configuration. A radioisotope is place either inside the expansion member, alloyed into the metal from which the expansion member is constructed, coated onto the expansion member's exterior surface or alternately, the non-radioactive metal or alloy of the expansion member can be irradiated so that it has become radioactive, i.e. it is then a radioisotope. The present method comprises the steps of advancing the radioactive expansion member or radioactive catheter to the obstruction in a vessel and applying opposed forces on said expansion member in an axial direction to move the expansion member to an expanded configuration wherein the expansion member dilates the obstruction and the catheter/expansion member assembly irradiates the obstruction.

41 Claims, 5 Drawing Sheets

241 231c 233 247 251 246 231c 231 14 248 253 242 26 26 234 17 17 236 237 14

21
42
88
86a
86
36
89
91
35
87
81
41
12
26
106
31
103
102
101
107
132
112
111

232
231a
222
11
11
223
221
262
231a
231b
231
263
264
261
266
268
267
269
231a
271
26
231b
231c
241
243
26
253
13
248
246
247
13
259
224
12
12
222

26
242
253
248
14
14
237
231
236
231c
246
17
17
251
247
233
231c
234
241
26

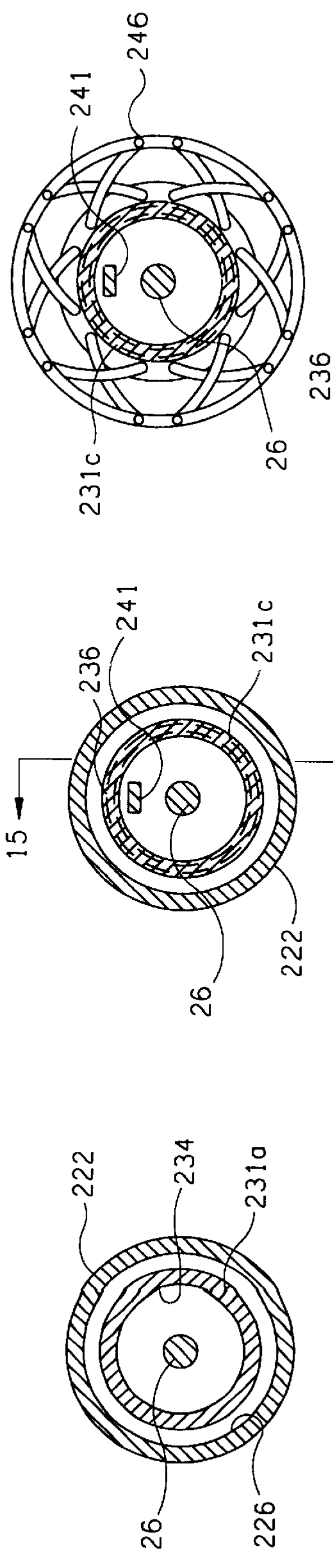
246
241
231c
26
236
FIG. 14
236
241
231c
15
15
26
222
FIG. 12
222
234
231a
26
226
FIG. 11
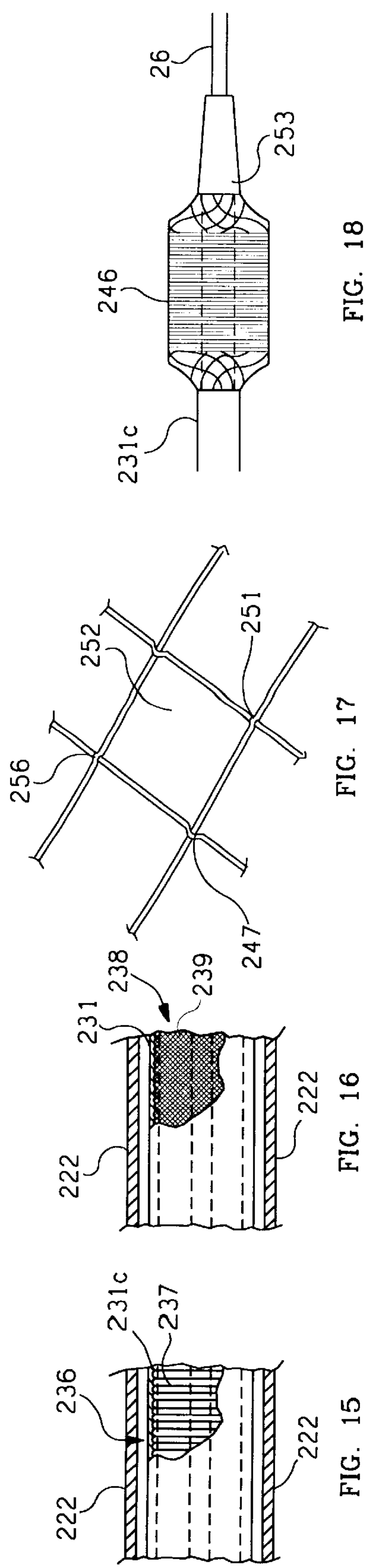
26
253
246
231c
FIG. 18
252
251
256
247
FIG. 17
231
238
239
222
222
FIG. 16
231c
237
236
222
222
FIG. 15

11a
11b
12
15
21
26
36
280
282
284
285
287
288
289

MECHANICAL APPARATUS AND METHOD FOR DILATING AND IRRADIATING A SITE OF TREATMENT

PRIOR APPLICATIONS

This application is a continuation-in-part of application Ser. No. 08/647,696 filed on May 15, 1996 now U.S. Pat. No. 5,755,708 which is a continuation-in-part of application Ser. No. 08/569,579 filed on Dec. 8, 1995 now U.S. Pat. No. 5,695,469 which is a continuation-in-part of application Ser. No. 08/353,558 filed on Dec. 9, 1994 now U.S. Pat. No. 5,527,282.

FIELD OF THE INVENTION

In general, the present invention relates to percutaneous transluminal devices and methods which are used treat obstructed (sclerotic) vessel lumina in humans. In particular, this invention relates to a mechanical apparatus and method for dilating an obstruction within an vessel while simultaneously and uniformly exposing the vessel segment to radioactive source. The mechanical dilation device can remain in this expanded configuration after the dilatation procedure is complete and continue exposing the vessel segment to the radioactive source. Furthermore, the present invention permits a continuous flow of blood during the entire procedure, including the extended period of exposure of the obstruction to further radiation therapy.

BACKGROUND OF THE INVENTION

Cardiovascular disease is commonly accepted as being one of the most serious health risks facing our society today. Diseased and obstructed coronary arteries can restrict the flow of blood and cause tissue ischemia and necrosis. While the exact etiology of sclerotic cardiovascular disease is still in question, the treatment of narrowed coronary arteries is more defined. Surgical construction of coronary artery bypass grafts (CABG) is often the method of choice when there are several diseased segments in one or multiple arteries. Open heart surgery is, of course, very traumatic for patients. In many cases, less traumatic, alternative methods are available for treating cardiovascular disease percutaneously. These alternate treatment methods generally employ various types of percutaneous transluminal angioplasty (PTCA) balloons or excising devices (atherectomy) to remodel or debulk diseased vessel segments. A further alternative treatment method involves percutaneous, intraluminal installation of expandable, tubular stents or prostheses in sclerotic lesions.

A recurrent problem with the previous devices and PTCA procedures is their failure to maintain patency due to the growth of injured vascular tissue. This is known as "restenosis" and may be a result of the original injury to the vessel wall occurring during the angioplasty procedure. Pathologically restenosis represents a neointimal proliferative response characterized by smooth muscle cell hyperplasia that results in reblockage of the vessel lumen necessitating repeat PTCA procedures up to 35–50% of all cases. It has been generally accepted that a radioisotope source may be capable of selectively inhibiting the growth of these hyperproliferating smooth muscle cells and thereby reduce the rate of restenosis after the primary interventional procedure.

Heretofore, various devices have been disclosed which may be used to expose a blood vessel undergoing angioplasty to intravascular radiation therapy. Balloon angioplasty catheters have been used to place and deploy a radioactive stent or prosthesis within human vessels. For example, in U.S. Pat. Nos. 5,059,166 and 5,176,617 a stent containing a radioactive source for irradiating an arterial segment to prevent restenosis is disclosed. In U.S. Pat. No. 5,199,939 an intravascular catheter and method for providing a radioactive means to the treated vessel segment is disclosed. In U.S. Pat. No. 5,616,114, an angioplasty balloon capable of inflation with a radioactive liquid for treatment of the affected vessel is described. U.S. Pat. No. 5,618,266 discloses a catheter for treating restenosis which contains a radioactive treatment source wire therein.

There are several disadvantages using either a stent or balloon catheter to uniformly expose a vascular segment to radiation. Regarding the radioactive stent, once the stent is deployed, there is no means outside of invasive surgical excision, to remove the radioactive source from the vascular segment. Therefore, stents or implanted prostheses with radioactive properties must employ a radioisotope whose half-life and penetration properties must be precisely calibrated to deliver an exact quantity of radiation to the vascular segment upon stent deployment. Balloon catheters employed to irradiate a vascular segment have limitations including potential balloon rupture and ischemia due to the fact that balloons cannot be inflated within the vessel for long periods of time because it interrupts the flow of blood to distal vessels. This leads to tissue ischemia and potential necrosis. Even "perfusion" type angioplasty balloons used to deliver a radiation source to the affected artery provide far less than physiological blood flow during balloon inflation and dwell times are limited by ischemia and tissue necrosis. Simple intravascular catheters used to deliver alpha, beta or gamma radioactive source wire to the affected vessel do not permit centering of the radioactive source uniformly within the vessel lumen and therefore deliver radiation which is undesirably unequal to different walls of the vessel. Lack of centering the radiation source may provide up to four (4) times the radioactive dose to the vessel wall nearer the source than the wall farther from the source.

Thus, it can be seen that there is a need for a new and improved device to selectively irradiate an arterial segment and which overcomes these disadvantages.

In general, it is an object of this present invention to provide a mechanical dilatation device and method which is capable of dilating an obstruction within a vascular segment while providing radiation to the vessel segment.

Another object of the invention is to provide a percutaneous device and method of the above character which can be used for prolonged periods in exposing a vascular segment to an intravascular radiation source while allowing continuous perfusion of blood into the distal to the treatment area.

Another object of the invention is to provide a device that is not susceptible to structural damage (balloon rupture) and subsequent release of radioactive materials into the vasculature.

A further object of the invention is to provide a device and method capable of providing a uniform dose of radiation to the vascular segment while dilating an obstruction within the vessel segment.

SUMMARY OF THE INVENTION

It is known that radiation therapy can reduce the proliferation of rapidly growing cells. The present invention utilizes a radioisotope source with a mechanical dilatation device for enlarging a flow passage of a vessel by dilating and irradiating an obstruction in the vessel. Since the radioisotope source is capable of selectively inhibiting the growth of hyperproliferating cells, the present invention not only achieves acute patency of a vessel but employs radiation therapy to maintain chronic patency through the prevention of restenosis.

The present invention comprises a substantially cylindrically shaped expansion member and includes a means engaged to the expansion member for altering the distance between the proximal end and the distal end of the expansion member thereby transforming the expansion member between a diametrically contracted configuration and a diametrically expanded configuration. A radioisotope may be placed either inside the expansion member, alloyed into the metal from which the expansion member is constructed, coated onto the expansion member's exterior surface or alternately, the non-radioactive metal or alloy of the expansion member can be irradiated so that it becomes radioactive, i.e. it is then a radioisotope. The radioisotope can be an alpha, beta or gamma emitter, or any combination of these radiation sources.

The present method comprises the steps of advancing the radioactive expansion member or radioactive catheter to the obstruction in a vessel and applying opposed forces on said expansion member in an axial direction to move the expansion member to an expanded configuration wherein the expansion member dilates the obstruction and the catheter/expansion member assembly irradiates the obstruction.

BRIEF DESCRIPTION OF THE DRAWINGS

FIG. 11 is an enlarged cross-sectional view taken along the line 11—11 of FIG. 10.

FIG. 12 is an enlarged cross-sectional view taken along the line 12—12 of FIG. 10.

FIG. 14 is a cross-sectional view taken along the line 14—14 of FIG. 13.

FIG. 15 is a cross-sectional view taken along the line 15—15 of FIG. 12.

FIG. 16 is a cross-sectional view similar to FIG. 15 but showing the use of a braid rather than a coil spring.

FIG. 17 is a greatly enlarged fragmentary view taken along the line 17—17 of FIG. 27.

FIG. 18 is a side-elevational view of the distal extremity of the device shown in FIGS. 10–14 showing the distal extremity with the expansion member in an expanded condition.

DETAILED DESCRIPTION OF THE DRAWINGS

Figures 1, 2, 3, 4, 5, 6, 7:
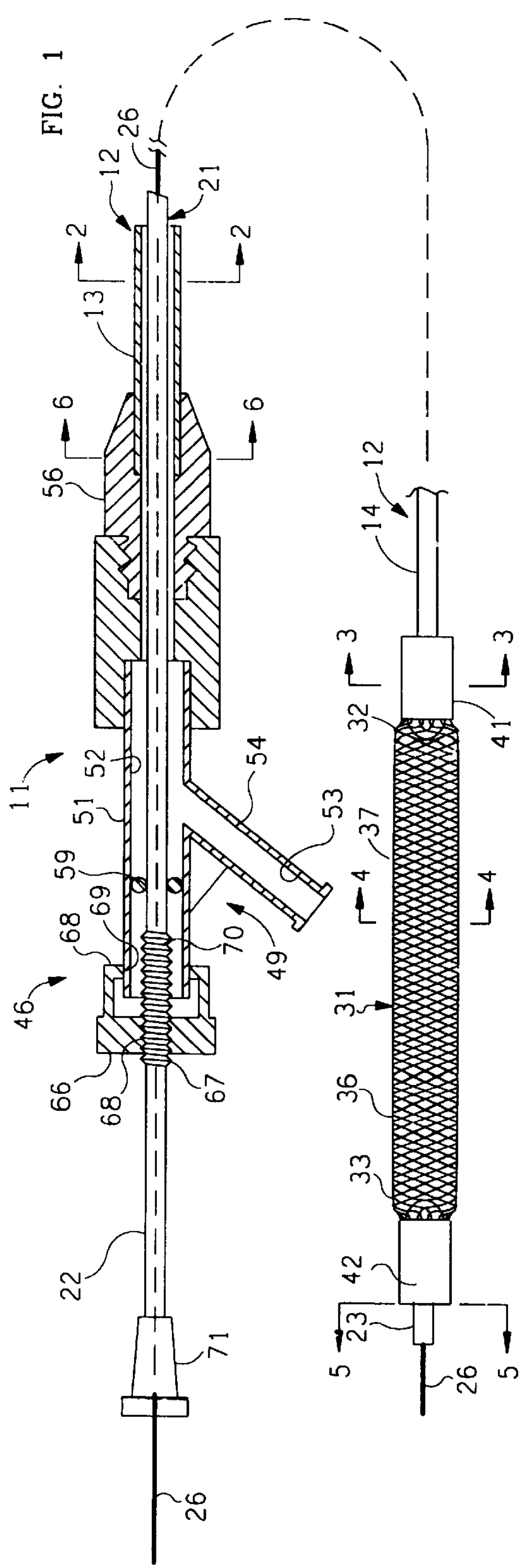
FIG. 1 is a side-elevational view partially in section of a mechanical dilatation and irradiation device incorporating the present invention.
FIG. 2 is a cross-sectional view taken along the line 2—2 of FIG. 1.
FIG. 3 is a cross-sectional view taken along the line 3—3 of FIG. 1.
FIG. 4 is a cross-sectional view taken along the line 4—4 of FIG. 1.
FIG. 5 is a cross-sectional view taken along the line 5—5 of FIG. 1.
FIG. 6 is a cross-sectional view taken along the line 6—6 of FIG. 1.
FIG. 7 is a greatly enlarged view of a portion of the dilatation and irradiation device in a partially expanded state.

In general, the present invention relates generally to devices which are used to dilate and irradiate an obstruction within a stenotic segment of a vessel. The device is comprised of an expansion member to be disposed in an obstruction in a vessel carrying flowing blood. The expansion member has first and second ends and an intermediate portion between the first and second ends. The expansion member also has a flow passage extending therethrough with a diameter and a longitudinal central axis. The diameter of the flow passage is a variable with movement of the first and second ends relative to each other along the longitudinal central axis from a diametrically contracted position to a diametrically expanded condition. The cylindrical expansion member is comprised of a plurality of flexible elongate elements each of which extends helically about the longitudinal extending central axis. In one embodiment of the present invention, a radiation source is located within the distal end of the device comprising a plurality of bands secured to the central axis that are either alloyed from a radioactive material or fabricated with a material that can subsequently become radioactive. In another embodiment, the flexible elongate elements are either alloyed with a radioactive material or fabricated with a material that can subsequently become radioactive. A plurality of the flexible elongate elements having a first common direction of rotation are axially displaced relative to each other and cross a further plurality of the flexible elongate elements also axially displaced relative to each other but having a second common direction opposite to that of the first direction of rotation to form a braided cylindrical expansion member. The crossing of the flexible elongate elements occurs in an area of contact between the flexible elongate elements. First and second means is provided respectively engaging the first and second ends of said cylindrical expansion member for retaining said first and second ends in contracted positions. Means is provided for causing relative axial movement of the first and second ends towards each other to cause the intermediate cylindrical portion of the expansion member to contact longitudinally and to expand diametrically by causing the flexible elongate elements in the intermediate portion of the cylindrical member to move closer to each other expanding the diametric dimensions of the cylindrical expansion member thereby expanding the surrounding prosthesis within an obstruction in the vessel. Flexible elongate elements at the first and second ends of the cylindrical expansion member remain contracted around and within first and second means and are thereby prevented from moving closer which maintains spacing between the flexible elongate members so that blood in the vessel can continue to flow through the first and second ends and through the flow passage in the cylindrical expansion member while the cylindrical expansion member is in engagement with the prosthesis and obstruction in the vessel. Due to the interdigitated surface configuration of the expansion member interacting with the inner surface of the stent or prosthesis, frictional and some mechanical interlocking forces will be present to suppress the stent or prothesis from shifting axially, rotating, or separating from the expansion member.

More in particular as shown in FIGS. 1–7 of the drawings which show the presence of the prosthesis secured on the present invention, the mechanical dilatation and irradiation device 11 shown therein consists of a first or outer flexible elongate tubular member 12 having proximal and distal extremities 13 and 14 with the flow passage 16 extending from the proximal extremity 13 to the distal extremity 14. A second or inner flexible tubular member 21 is coaxially and slidably disposed within the flow passage 16 of the first or outer flexible elongate tubular member 12 and is provided with proximal and distal extremities 22 and 23 with a flow passage 24 extending from the proximal extremity 22 to the distal extremity 23.

A guide wire 26 of a conventional type is adapted to be introduced through the flow passage 24 in the inner flexible elongate tubular member for use in guiding the mechanical dilatation and irradiation device 11 as hereinafter described. The guide wire 26 can be of a suitable size as for example 0.010"–0.035" and can have a suitable length ranging from 150 to 300 centimeters. For example, the first or outer flexible elongate tubular member 12 can have an outside diameter of 0.6–3 millimeters with a wall thickness of 0.12 millimeters to provide a flow passage of 0.75 millimeters in diameter. Similarly, the second or inner flexible elongate tubular member 21 can have a suitable outside diameter as for example 0.6 millimeters with a wall thickness of 0.12 millimeters and a flow passage 24 of 0.45 millimeters in diameter. The flexible elongate tubular members 12 and 21 can be formed of a suitable plastic as for example a polyimide, polyethylene, Nylon or polybutylterphalate (PBT).

In accordance with the present invention an expansion member 31 is provided which has a first or proximal end 32 and a second or distal end 33 with a central or inner flow passage 34 extending from the proximal end 32 to the distal end 33 along a longitudinally extending central axis and has a diameter which is a variable as hereinafter described. The expansion member 31 is comprised of a plurality of flexible elongate elements or filaments 36 each of which extends helically about the longitudinally extending central axis. The flexible elongate elements 36 are formed of suitable materials which can be utilized in the human blood as for example stainless steel, Nitinol, Aermet™, Elgiloy™ or certain other plastic fibers. The flexible elongate elements 36 can have a suitable diameter as for example 0.001 to 0.010 inches or can be configured as a round, elliptical, flat or triangular wire ribbon. A plurality of the flexible elongate elements 36 have a first common direction of rotation about the central axis as shown in FIGS. 1, 7, 8 and 15 are axially displaced relative to each other and cross a further plurality of the flexible elongate elements 36 also axially displaced relative to each other but having a second common direction of rotation opposite to that of the first direction of rotation to form a double helix or braided or mesh-like cylindrical expansion member with the crossing of flexible elongate elements 36 occurring in the area of contact between the flexible elongate elements to form openings or interstices 37 therebetween. Thus the flexible elongate elements 36 form an expansion member 31 which provides a central or inner flow passage 34 which is variable in diameter upon movement of the first and second ends of the expansion member 31 relative to each other along the longitudinally extending central axis. As shown in FIGS. 8, 11, and 15 through 20 of the drawings, an expandable stent or prosthesis 45 is intended to be placed on and secured to the expansion member 31.

Means is provided for constraining the first and second or proximal and distal ends 32 and 33 of the expansion member 31 and consists of a first or proximal collar 41 and a second or distal collar 42. The first and second collars 41 and 42 are formed of a suitable material such as a polyimide. The first or proximal collar 41 has a suitable length as for example 1.0 to 5.0 millimeters and is sized so that it can fit over the first or proximal end 32 of the expansion member 31 when it is in a contracted position and over the distal extremity 14 of the first or outer flexible elongate member 12. In order to ensure that elongate elements or filaments 36 of the first or proximal extremity 32 are firmly secured to the distal extremity 14 of the first or outer flexible elongate member 12, an adhesive can be provided bonding the first or proximal end 32 to the collar 41 and to the distal extremity 14 of the first or outer flexible elongate tubular member 12. The second or distal collar 42 can be of a suitable size and typically may be slightly smaller in diameter because it need merely secure the elongate element or filaments 36 of the distal end 33 of the expansion member 31 to the distal extremity 23 of the second or inner flexible elongate tubular member 21. An adhesive (not shown) is provided to firmly secure the second or distal end 33 of the expansion member 31 between the second or distal collar 42 and the distal extremity of the inner flexible elongate tubular member 21. In this manner it can be seen that the cylindrical expansion member 31 has its proximal end curved conically inward toward and secured to the distal extremity of the outer flexible elongate tubular member 12 and the second or distal end 33 of the expansion member 31 also curves conically inward toward and is secured to the distal extremity of the second or inner flexible elongate tubular member 21.

Typically the distance between the first and second collars 41 and 42 can range from between 5 to 150 millimeters. Typically the distal end 23 of the second or inner flexible elongate tubular member 21 extends approximately 5–170 millimeters beyond the distal extremity 14 of the first or outer flexible elongate tubular member 12.

It can be seen that by moving the first or outer flexible elongate tubular member 12 and the second inner flexible elongate tubular member 21 axially with respect to each other, the first and second ends of the expansion member 31 are moved towards each other causing the elongate elements or filaments 36 of an intermediate portion of the cylindrical expansion member between the first and second ends to move closer to each other to cause these flexible elongate elements to move into apposition with each other and to expand in a first radial direction the intermediate portion of the cylindrical expansion member 31 (FIG. 7) and to cause the diameter of the central flow passage 34 to increase. The portions of the expansion member 31 immediately adjacent the first and second collars 41 and 42 remain restrained by the collars 41 and 42 causing the flexible elongate elements 36 immediately adjacent to the collars 41 and 42 to curve conically toward and remain crossed and unable to come into close apposition and thereby provide openings or interstices 37 therebetween, which remain relatively constant in shape and size so that blood can flow from the first and second ends 32 and 33 through the central or inner flow passage 34 as hereinafter described.

Means is provided in the mechanical dilatation and irradiation device 11 for causing relative movement between the first or outer flexible elongate tubular member 12 and the second or inner flexible elongate tubular member 21 and consists of a screw mechanism 46. The screw mechanism 46 includes a Y-adapter 49 which is provided with a central arm 51 having a lumen 52 through which the second or inner flexible elongate tubular member 21 extends. The lumen or flow passage 52 is in communication with the lumen 16 of outer flexible elongate tubular member 12 and with a flow passage 53 in a side arm 54 which is adapted to receive a syringe (not shown) so that saline, radiocontrast liquid or a drug can be introduced through the side arm 54 and into the flow passage 52 in the Y-adapter 49 and thence into lumen 16 of outer member 12. The distal end of screw mechanism 46 is provided with a fitting 56 with inner lumen 57 (see FIG. 6) into which the proximal end 13 of flexible elongate tubular member 12 is seated and held in place by an adhesive 58 at the distal end of fitting 56. Lumen 57 is thereby in communication with flow passage 52 of central arm 51 and with flow passage 53 of side arm 54. An O-ring 59 which is adapted to form a fluid-tight seal with respect to the second or inner flexible tubular member 21 is disposed in the lumen 52 of the central arm 51. An interiorly threaded knurled knob 66 is threaded onto an exteriorly threaded member 67 which is secured to and surrounds the proximal extremity 22 of inner flexible elongate tubular member 21. The knob 66 is provided with an inwardly extending flange 68 which seats in an annular recess 69 in the central arm 51. Thus, rotation of the knob 66 causes advancement or retraction of threaded member 67 and the second or inner flexible elongate tubular member 21 with respect to the fitting 56. Indicia 68 in the form of longitudinally spaced-apart rings 70 are provided on the member 67 and serve to indicate the distance which the second or inner flexible elongate tubular member 21 has been advanced and retracted with respect to the first or outer flexible elongate member 12.

A Luer-type fitting 71 is mounted on the proximal extremity 22 of the inner elongate flexible tubular member 21 and is adapted to be engaged by a finger of the hand. The guide wire 26 extends through the fitting 71 and into the lumen 24 of inner elongate flexible tubular member 21.

It should be appreciated that even though one particular screw mechanism 46 has been provided for advancing and retracting the flexible elongate members 12 and 21 with respect to each other, other mechanisms also can be utilized if desired to provide such relative movement. Other possible designs that could be employed are scissors-jack, rachet-type or straight slide mechanisms.

In order to provide the desired radiopacity for the distal extremity of the mechanical dilatation and irradiation device 11 so that it can be observed fluoroscopically during a dilatation procedure, the collars 41 and 42 can be formed of a radiopaque material as for example by filling the polymeric material with radiopaque particles of a suitable material such as barium or by providing collars containing radiopaque metals, such as tungsten or platinum or a tungsten/platinum alloy. Although the flexible elongate elements 36 which comprise the expansion member 31 have some radiopacity by being formed of a stainless steel or other suitable material such as Elgiloy, there normally is insufficient radiopacity for most medical procedures. Therefore to augment the radiopacity of the expansion member 31, radiopaque wire of a suitable material such as platinum or tungsten can be wound along with the flexible elongate element 36 to provide the necessary radiopacity. This often may be desirable because this would make it possible to ascertain the position of the cylindrical expansion member and its diameter as it is expanded and retracted between a minimum contracted position and a maximum expanded position by relative movement between the distal extremities of the first or outer flexible elongate member 12 and the second or inner flexible elongate tubular member 21. The use of the helical wraps of platinum does not significantly interfere with the general mechanical properties of the expansion member 31 desired in connection with the present invention. Alternatively, the flexible elongate elements 36 may be plated with a radiopaque metal such as platinum or gold to enhance their radiopacity. Alternatively, the flexible elongate elements may be comprised of hollow wires, the central core of which may be filled with radiopaque metals such as tungsten, gold or platinum or with compound salts of high radiopacity.

To perform as a radioactive source for the present invention, the flexible elongate elements themselves can be radioactive as described in more detail below. The flexible elongate elements may be alloyed from a material, coated with a material, or have a central lumen that can be filled with a material, that becomes radioactive by exposure to a particular isotope utilizing one of the activation mechanisms known by those skilled in the art. Alternatively, the flexible elongate elements may be alloyed from a material, coated with a material, or have a central lumen that can be filled with a material, that is radioactive (presently undergoing nuclear decay).

Operation and use of the mechanical dilatation and irradiation device 11 may now be briefly described as follows. Let it be assumed that the patient which the medical procedure is to be performed utilizing the mechanical dilatation and irradiation device 11 has one or more stenoses which at least partially occlude one or more arterial vessels supplying blood to the heart and that it is desired to enlarge the flow passages through these stenoses. Typically the mechanical dilatation and irradiation device 11 would be supplied by the manufacturer with the cylindrical expansion member 31 in its most contracted position to provide the lowest possible configuration in terms of diameter and so that the diameter approximates the diameter of the outer flexible elongate tubular member 12. Thus, preferably, it should have a diameter which is only slightly greater than the tubular member 12, as for example by 1.0–2.3 millimeters. The first and second collars 41 and 42 also have been sized so they only have a diameter which is slightly greater than the outer diameter of the outer flexible elongate tubular member 12. To bring the cylindrical expansion member 31 to its lowest configuration, the screw mechanism 46 has been adjusted so that there is a maximum spacing between the distal extremity 23 of the inner flexible elongate tubular member 21 and the distal extremity 14 of the outer flexible elongate tubular member 12. In this position of the expansion member 31, the flexible elongate elements 36 cross each other at nearly right angles so that the interstices or openings 37 therebetween are elongated with respect to the longitudinal axis.

The mechanical dilatation and irradiation device 11 is then inserted into a guiding catheter (not shown) typically used in such a procedure and introduced into the femoral artery and having its distal extremity in engagement with the ostium of the selected coronary artery. Thereafter, the guide wire 26 can be inserted independently of the mechanical dilatation and irradiation device 11. If desired the guide wire 26 can be inserted along with the mechanical dilatation and irradiation device 11 with its distal extremity extending beyond the distal extremity of device 11. The guide wire 26 is then advanced in a conventional manner by the physician undertaking the procedure and is advanced into the vessel containing a stenosis. The progress of the distal extremity of the guide wire 26 is observed fluoroscopically and is advanced until its distal extremity extends distally of the stenosis. with the expansion member 31 in its diametrically contracted position and the prosthesis secured thereon, the mechanical dilatation and irradiation device 11 is advanced over the guide wire 26. The distal extremity 23 of the second or inner flexible elongate tubular member 21 is advanced through the stenosis over the guide wire 26 until it is distal to the stenosis and so that the distal extremity 14 of the first or outer flexible elongate tubular member 12 is just proximal of the stenosis.

After the expansion member 31 is in a desired position in the stenosis, the expansion member 31 is expanded from its diametrically contracted position to an expanded position by moving the distal extremities 14 and 23 closer to each other by operation of the screw mechanism 46. This can be accomplished by holding one distal extremity stationary and moving the other distal extremity towards it or by moving both distal extremities closer to each other simultaneously. This movement of the distal extremities 14 and 23 causes collars 41 and 42 to move closer to each other and to cause the central flexible elongate elements 36 forming the double helix mesh of the intermediate portion 31*a* of the flexible cylindrical expansion member 31 to move relative to each other to progressively decrease the vertical crossing angle of the double helically wound flexible elongate elements 36 from approximately 140° to 170° in its extended state to 5° to 20° in its axially contracted state and to progressively change the interstices or openings 37 from diamond-shaped openings with long axes parallel to the central longitudinal axis of the catheter in its extended state to substantially square-shaped openings in its intermediately contracted state to elongate diamond-shaped interstices or openings with the longitudinal axes extending in directions perpendicular to the central longitudinal axis with the flexible elongate elements 36 coming into close apposition to each other while at the same time causing radial expansion of the expansion member and to progressively increase the diameter of the central flow passage 34. The enlargement of expansion member 31 in addition to being viewed fluoroscopically can also be ascertained by the indicia 68 carried by the threaded member 67.

During the time that the expansion member 31 is being expanded, it exerts radial forces against the vessel wall or alternately a stent, thereby expanding the wall or stent against the stenosis. If employed, the prosthesis compresses against and becomes implanted within the wall of the vessel thereby enlarging the stenosis so that an increased amount of blood can flow through the vessel. The intermediate portion 31*a* of the expansion member 31 when fully expanded is almost a solid tubular mass which has significant radial strength to fully expand the stent or prosthesis. In addition, because of spring-like properties of the enlarged expansion member being comprised of helically wound flexible elongate elements 36, the expansion member 31 can conform to a curve within the blood vessel while still exerting significant radial force to the stent or prosthesis and to make possible compression of the stenosis without tending to straighten the curve in the vessel which typically occurs with standard straight angioplasty balloon systems. Since the expansion member can be comprised of flexible elongate elements that themselves are a radiation source (see FIG. 22), or alternatively have a hollow core containing a radiation source (see FIG. 23), or alternatively are coated with a radiation source, uniform alpha, beta, or gamma radiation can be delivered to the vessel during the time of device expansion (see FIGS. 20, 25).

Since the ends of the expansion member 31 are constrained by the proximal and distal collars 41 and 42, the flexible elongate elements 36 form a braided mesh of the expansion member 31 adjacent to the distal extremity 23 of the inner elongate flexible tubular member 21 and the distal extremity 14 of the outer flexible elongate tubular member 12 under the collars 41 and 42, respectively, are held in substantially constant angular relationship to each other with the vertical crossing angles between 5° and 17° and are unable to come into close apposition with each other. Therefore the interstices or openings 37 adjacent the collars 41 and 42 remain open because the flexible elongate elements 36 are unable to change from their relatively fixed crossed positions. Blood continues to flow through the central or inner flow passage 34 by passing through the openings 37 in the first or proximal end 32 into the central or inner passage 34 and out the openings in the second or distal end 33. Thus, blood flow through the vessel is not impeded by the expansion of the expansion member 31. It is believed that the flow through the central or inner flow passage 34 can be significantly greater than that which can be provided with a standard perfusion balloon.

Since blood flows continuously through the dilatation and irradiation device during the dilatation and irradiation procedure, there is minimal danger of ischemia occurring. This makes it possible to maintain dilatation and irradiation of the obstruction over extended periods of time when desired. One particularly advantage for the mechanical dilatation and irradiation device 11 is that it could be used with patients which have obstructions of a critical nature that cannot even tolerate relatively short periods of balloon dilatation without leading to ischemia creating permanent damage or shock to the patient. Another advantage of the present invention is that uniform exposure of radiation to the vessel wall can be accomplished during this time.

The open construction of the expansion member 31 also serves to prevent blocking off of other vessels branching off from the vessel in the region in which dilatation and irradiation procedures are being performed because the blood can flow through the central interstices 38 of the expansion member 31.

After dilatation and irradiation of the lesion has been carried out for an appropriate length of time, the expansion member 31 can be moved from its expanded position to a contracted position by operation of the screw mechanism 46 in a reverse direction to cause separation of the distal extremities 14 and 23 to thereby cause elongation of the expansion member 31 with a concurrent reduction in diameter.

After the expansion member 31 has been reduced to its contracted or minimum diameter, the mechanical dilatation and irradiation device 11 can be removed along with the guide wire 26 after which the guiding catheter (not shown) can be removed and the puncture site leading to the femoral artery closed in a conventional manner.

Although, the procedure hereinbefore described was for treatment of a single stenosis, it should be appreciated that if desired during the same time that the mechanical dilatation and irradiation device 11 is within the guiding catheter, other vessels of the patient having stenoses therein can be treated in a similar manner merely by retracting the distal extremity of the mechanical dilatation and irradiation device 11 from the stenosis being treated, placing another prosthesis over the expansion member, and then advancing it into another stenosis in another vessel in a similar manner.

Figures 8, 9, 9A:
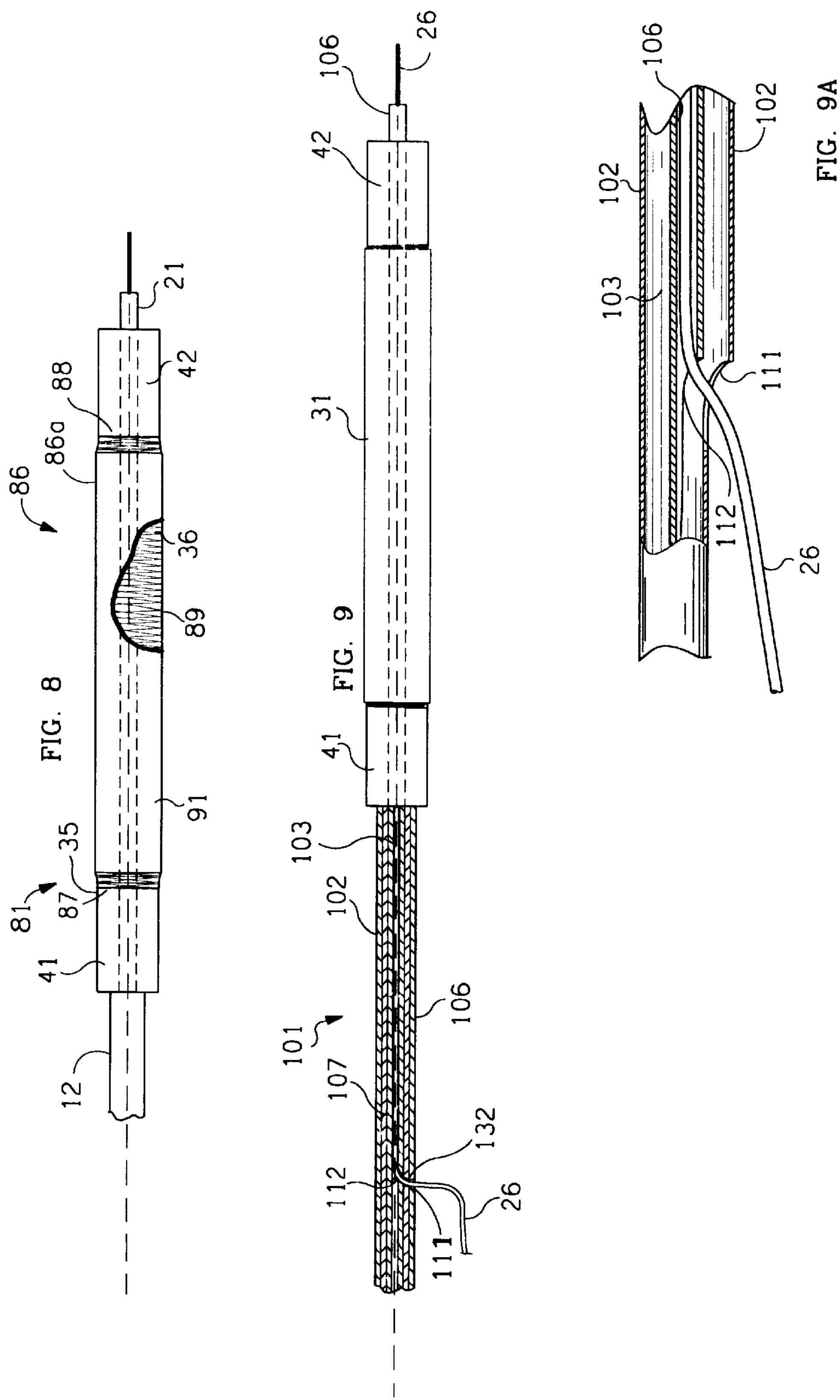
FIG. 8 is a partial side-elevational view of another embodiment of a mechanical dilatation and irradiation device incorporating the present invention with a part of the device covered by a protective material to prevent damage to the vessel wall.
FIG. 9 is a partial side-elevational view of another embodiment of a mechanical dilatation and irradiation device incorporating the present invention which can be utilized in conjunction with a rapid exchange technique.
FIG. 9*a* is an enlarged side-elevational view of the rapid exchanged embodiment of the mechanical dilatation and irradiation device demonstrating the guidewire entry ports in the inner and outer elongated tubular members.

Another embodiment of a mechanical dilatation and irradiation device of the present invention is shown in FIG. 8 in which the mechanical dilatation and irradiation device 81 is very similar to the mechanical device 11 with the exception that the flexible cylindrical expansion member 86 is constructed in a different manner. As shown in FIG. 8, the flexible stainless steel expansion member 86 is formed of flexible elongate elements 36 in the manner hereinbefore described to provide a mesh construction having proximal and distal extremities 87 and 88 and having an intermediate portion 86*a* between the proximal and distal extremities 87 and 88 and a central flow passage 89 extending therethrough. The expansion member 86 differs from the expansion member 31 in that the outer surface of the intermediate portion 86*a* between the proximal and distal ends 87 and 88 carries and is covered or encapsulated with a radially expandable and contractible material 91 such as a latex, polyurethane, silicone or other thermoplastic elastomer. Such a flexible, expandable and contractible coating can be readily provided on the flexible cylindrical member 86 such as by placing the same on a mandrel (not shown) and masking off the proximal and distal extremities 87 and 88 by a suitable masking material and then dipping the expansion member into the desired coating material and then cured in an appropriate manner to bond the expandable-contractible material 91 to the flexible elongate elements 36. The coating material 91 applied encapsulates the flexible elongate elements 36 and fills in the interstices or openings 38 between the elements in the intermediate portion 86*a*. Alternatively, a tubular sleeve of the appropriate dimensions may be made from the latex, polyurethane, silicone or polymer material and then placed over the intermediate portion 86*a* of the cylindrical member 86 to leave the proximal and distal extremities 87 and 88 exposed. These proximal and distal extremities 87 and 88 can be secured to the distal extremities 14 and 23 by the collars of 41 and 42 in a manner similar that hereinbefore described.

A mechanical dilatation and irradiation device 81 constructed in this manner can be used in the same manner as the mechanical dilatation and irradiation device 11 and can be operated in the same manner. The coated intermediate portion 86*a* serves to protect the vessel wall from damage and prevents potential entrapment of tissue between the flexible elongate elements 36 as they are being compressed axially while still permitting the relative free passage of blood into proximal extremity 87 and into the central flow passage 89 and out distal extremity 89.

Another embodiment of a dilatation and irradiation device incorporating the present invention is shown in FIGS. 9 and 9*a*. As shown therein, the mechanical dilatation and irradiation device 101 is constructed in a manner similar to the mechanical dilatation and irradiation device 11 with the exception that it is provided with rapid exchange capabilities. This is accomplished by providing an outer flexible elongate tubular member 102 having a lumen 103 therein and an inner flexible elongate tubular member 106 having a lumen 107 which have the expansion member 31 secured thereto by the proximal and distal collars 41 and 42. The outer flexible elongate tubular member 102 is provided with a port or opening 111 into the corresponding lumen 103 and which is 13–60 centimeters from the distal extremity 32 of the expansion member 31. A corresponding port or opening 112 into corresponding lumen 107 is provided within the inner flexible elongate tubular member 106. These ports 111 and 112 are positioned so that when the expansion member 31 is in its expanded position with the distal extremities of the members 102 and 106 being in closest proximity to each other, the openings 111 and 112 are in registration with each other. In this position, the mechanical dilatation and irradiation device 101 can be loaded onto the guide wire 16 by advancing the most proximal extremity of guide wire 26 first into lumen 107 of the distal extremity of the inner flexible elongate member 106 and then back through port or opening 112 and port 111 which are in registration and out of the flexible elongate tubular member 102. The expansion member 31 is next contracted from its diametrically expanded condition to a contracted condition by moving the distal extremities of outer and inner flexible elongate tubular members 102 and 106 further apart by operation of screw mechanism 46. This procedure is performed while maintaining a stable position of the external position of guide wire 26 in a constant position in relation to port 111. As the distal extremity of flexible tubular member 106 is moved further from the distal extremity of flexible elongate tubular member 102, port 112 will move out of registration with port 111 while maintaining guide wire 26 within lumen 107 and advancing the distal extremity of the flexible elongate tubular member 106 along the guide wire 26. In this diametrically contracted state of the expansion member 31, the mechanical dilatation and irradiation device 101 may be advanced along guide wire 26 through the region of stenosis in the blood vessel and enlargement of expansion member 31 may occur using screw mechanism 46 in the manner previously described. Once dilatation and irradiation has been completed, expansion member 31 can be diametrically contracted and the mechanical dilatation and irradiation device 101 may be removed from the blood vessel and the guiding catheter by maintaining a stable position of guide wire 26 in relation to the blood vessel and retracting device 101 along guide wire 26 until the distal extremity of inner flexible member 106 exits the patient's body. The mechanical dilatation and irradiation device 101 may now be rapidly exchanged with another mechanical device 101 as for example, one having an expansion member 31 which can be increased to a larger diameter over a standard 175 to 185 centimeter length guide wire 26.

Another embodiment of a mechanical dilatation and irradiation device 221 incorporating the present invention is shown in FIGS. 10–16. As shown therein, the device 221 consists of a flexible elongate tubular member 222 having proximal and distal extremities 223 and 224. The flexible elongate tubular member 222 can be formed out of a suitable material such as a polyethylene or a polyimide.

A lumen 226 extends from the proximal extremity 223 to the distal extremity 224 and has a size which is the same as in the first or outer flexible elongate tubular member 12 hereinbefore described in connection with the previous embodiments. Thus, it can have a suitable size as for example 3–5 French. A second or inner flexible elongate tubular member 231 is provided which is slidably and coaxially disposed within the lumen 226. It is provided with proximal and distal extremities 232 and 233 with a lumen 234 extending from the proximal extremity 232 to the distal extremity 233. In the present embodiment of the invention, the inner flexible elongate tubular member 231 serves as a support member. The flexible elongate tubular member 231 is formed of three portions 231*a*, 231*b* and 231*c* with the first portion 231*a* being at the proximal extremity 232 and the second portion 231*b* extending from the proximal extremity 232 to the near distal extremity 233. The portion 231*a* is formed of a hypotube having an outside diameter of 0.010" to 0.042" and an inside diameter of 0.012" to 0.030" to provide a wall thickness of 0.002" to 0.010". The portion 231*a* has a suitable length as for example 10–30 centimeters. The second portion 231*b* can be formed so that it has an outside diameter of 0.016" to 0.042" and an inside diameter of 0.012" to 0.030" to provide a wall thickness of 0.002" to 0.010". Thus it can be seen that the portion 231*a* has a greater wall thickness and provides additional stiffness and rigidity. A guide wire 26 of the type hereinbefore described is slidably disposed in the lumen 234. The lumen 234 in the flexible elongate tubular support member 231 is sized so that it can readily accommodate the guide wire 26. Thus, if a guide wire having a size 0.014" is used, the lumen 226 should have a diameter which is greater than 0.016" to 0.018".

The third portion 231*c* of the flexible elongate tubular support member 231 is formed of a suitable material such as plastic, as for example a polyimide. It has a suitable length, as for example from 20–40 centimeters and preferably a length of approximately 30 centimeters. The portion 231*c* is bonded to the distal extremity of the portion 231*b* by suitable means such as an adhesive. In order to increase the pushability of the portion 231*c* of the flexible elongate tubular member 231 while retaining its flexibility, a coil spring 236 is embedded within the plastic forming the portion 231*c*. The coil spring 236 is provided with a plurality of turns 237 as shown in detail in FIG. 15, which preferably are immediately adjacent or in apposition to each other to provide for maximum pushability. The coil spring 236 should extend at least throughout the length of the cylindrical member mounted coaxially thereover as hereinafter described. In addition, as shown the coil spring 236 can extend the entire length of the portion 231*c*. The coil spring 236 is carried by the portion 231*c* and preferably can be embedded or encapsulated within plastic 238 of the same type forming the tubular support member 231. Such embedding of the coil spring 236 prevents uncoiling of the coil elements or turns 237 and elongation of the flexible elongate tubular member 231 upon retraction of the inner elongate tubular member 231 into the outer elongate tubular member 226 with decrease in distance between proximal and distal ends of the expansion member. Alternatively, as shown in FIG. 16, a braided member 238 may be substituted for the coil spring 236 and also encapsulated or embedded with the plastic forming portion 231*c*. Such encapsulation also prevents elongation of portion 231*c* upon retraction of the flexible elongate tubular support member 231 into the outer elongate tubular member 226. The metal braid 238 formed of a suitable material such as stainless steel wires 239 of a suitable diameter ranging from 0.0002" to 0.003" can be used to form the mesh for the braided member 238. The braided member 238 increases the pushability of the portion 231*c* of the inner flexible elongate tubular member 231 and also prevents substantial elongation of the inner flexible elongate tubular member 231. Furthermore, metal braid 238 can consist of flat ribbon.

A safety ribbon 241 is provided within the inner flexible tubular member 231 to prevent elongation of the portion 231*c* of the inner flexible elongate tubular member 231 and extends from the distal extremity of portion 231*b* to the distal extremity of portion 231*c*. The safety ribbon 241 can be formed of a suitable material such as stainless steel having a diameter area of 0.002" to 0.004" or a ribbon with a flat cross section. The safety ribbon 241 is disposed adjacent the portion 231*c* of the flexible elongate tubular member 231, and preferably as shown extends interiorly of the portion 231*c* in the lumen 234 and has its distal extremity secured to the distal extremity of the portion 231*c* by solder 242. The safety ribbon 241 has its proximal extremity secured to the distal extremity of the portion 231*b* of the inner flexible elongate tubular member 231 by the use of solder 242 (see FIG. 13).

Figure 10:
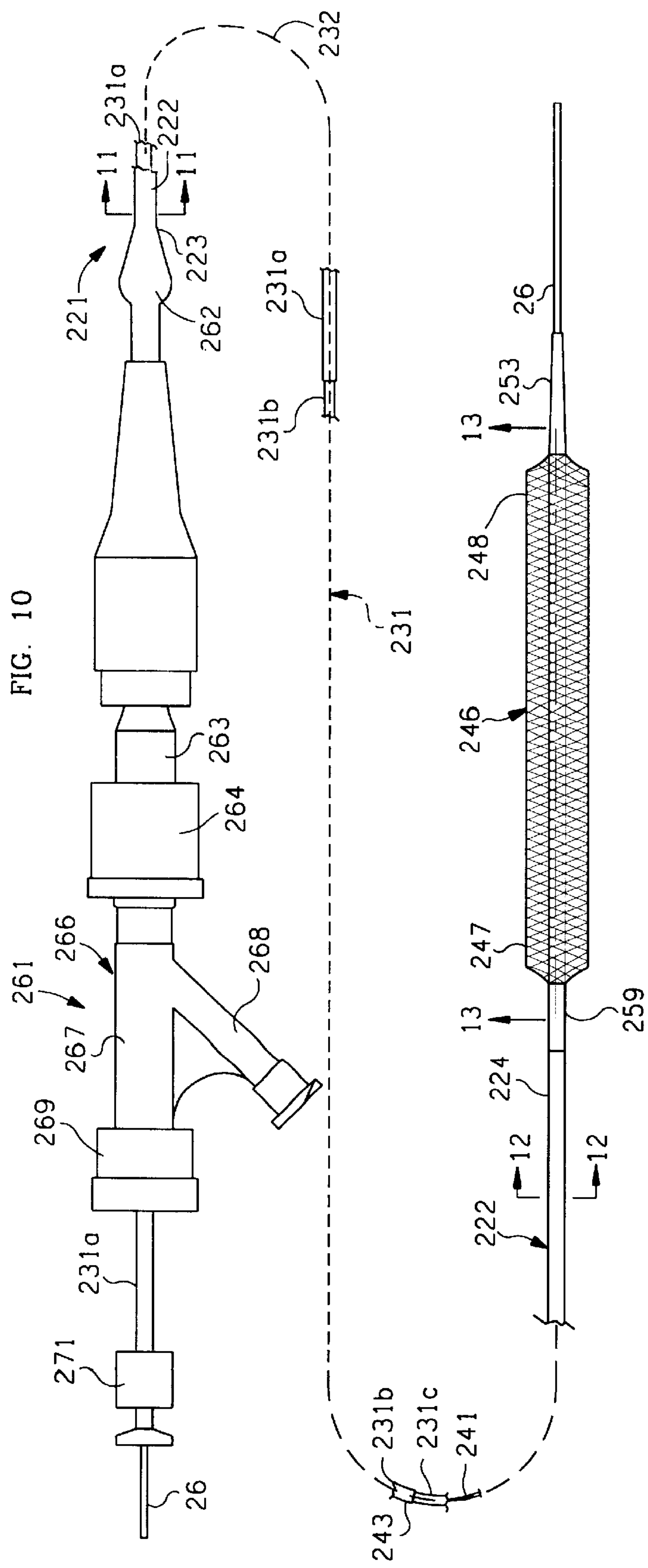
FIG. 10 is a side-elevational view partially in section of a mechanical dilatation and irradiation device incorporating another embodiment of the present invention.
Figure 13:
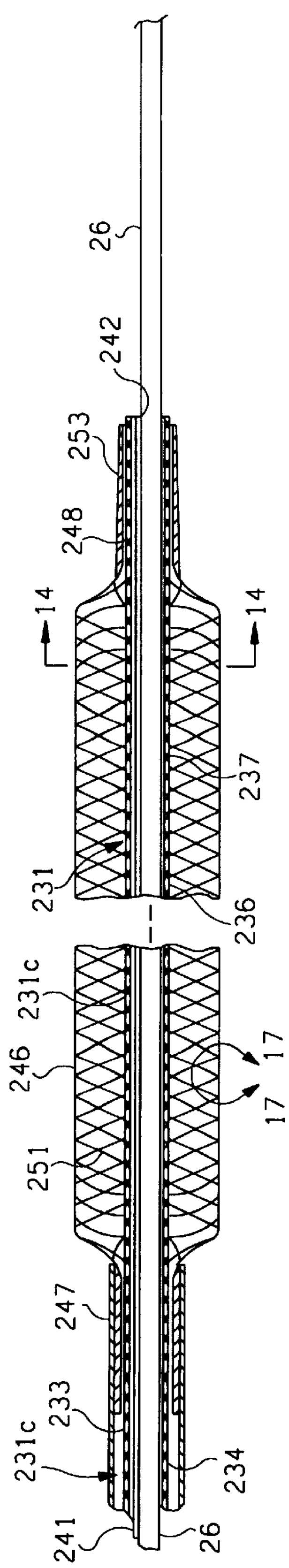
FIG. 13 is an enlarged side-elevational view of a portion of the device shown in FIG. 10 looking along the line 13—13.

An expansion member 246 is provided with proximal and distal extremities 247 and 248 as shown in FIG. 13 and is disposed coaxially on the portion 231 of the inner flexible elongate tubular member 231. The expansion member 246 is constructed in a manner similar to the expansion member 31 hereinbefore described and is provided with a plurality of flexible elongate elements or filaments 251 in which a plurality of elements 251 have a first common direction of rotation about the central axis as shown in FIG. 10 and are axially displaced relative to each other and cross over a further plurality of the flexible elongate elements 251 also axially displaced relative to each other but having a second common direction of rotation opposite to that of the first direction of rotation to form a double helix, braided or mesh-like cylindrical expansion member 246 with the crossing of the flexible elongate elements 251 occurring in the area of contact between the flexible elongate elements 251 to form openings or interstices 252 therebetween. The solder 242 used for securing the safety ribbon 238 to the coil spring 236 is also used for securing the distal extremity 248 of the cylindrical member 246 to the distal extremity of the inner flexible elongate tubular member 231. A sleeve 253 of heat shrink tubing covers the solder 242.

In order to increase the radial forces generated by the expansion member 246, it has been found that it is desirable to provide undulations 256 in which there is an undulation 256 present at each cross-over point of the filaments 251. Thus, as shown in FIG. 17, which is a fragmentary view of the cylindrical expansion member 246 shown in FIG. 13, an undulation 256 is provided in each of the plurality of flexible elongate elements 251 having a first direction of rotation at every other cross-over point with the plurality of flexible elongate elements having a second common direction of rotation about the central axis and wherein the undulations in the adjacent elements 251 are offset by one cross-over point so that in the resulting mesh or braid construction, the undulations 256 in one of the elements 251 having a first direction of rotation overlies every other cross-over point of the element 251 having a second direction of rotation and, conversely, every element 251 having a second direction of rotation has an undulation 256 therein at every other cross-over point of the elements 251 having a first direction of rotation. These undulations 256 can be in the form of obtuse angle bends having straight portions extending from both sides of the bend, or alternatively can be in the form of arcuate portions having a diameter corresponding generally to the diameter of the elements 251. Thus, it can be seen that the undulations 251 make it possible for one of the elements 251 to support the other of the elements at each cross-over point, thereby preventing slippage of the elements 251 with respect to each other and thereby causing greater radial forces to be applied when the cylindrical expansion member 246 is expanded as hereinafter described. Furthermore, alternate braid configurations can be employed. One such alternate configuration is two wires crossing two wires alternatively (known as a 2 over 2 braid), The expansion member 246 is comprised of 16–64 individual elements 251 formed of 0.001 to 0.005 inch diameter wire of a suitable metal such as stainless steel helically wound around a longitudinal central axis. The helices are wound in opposite directions. Stretching or elongation of the cylindrical expansion member 246 results in a reduction in diameter of the expansion member 246. Mechanical fixation of the proximal and distal extremities 247 and 248 of the expansion member 246 holds these extremities in reduced diameter configurations. The positions of the elements 251 in these extremities cannot change in relation to each other. Therefore, the crossing angles of the elements 251 remain constant. Shortening of the cylindrical expansion member 246 with the ends fixed results in the formation of a cylindrical center section of great rigidity with the elements 251 in close apposition to each other. The tapered proximal and distal extremities of the expansion member 246 causes the stresses on the individual elements 251 to be balanced. Since the proximal and distal extremities 247 and 248 are held in constant tapered positions, the interstices 252 between the elements 251 are maintained allowing blood to flow into and out of the cylindrical center section when the expansion member 246 is shortened as shown in FIG. 18. Shortening of the expansion member or spring 246 results in a significant increase in the metal density per unit length in the center portion of the expansion member 246 while the metal density at the ends is relatively constant. This increase in metal density in the center section results in significant radial force generation as the elements 251 are compressed in a longitudinal direction into preformed diameters.

Use of the helically wound coil spring 236 or the braid 238 which serves with or as part of the inner elongate tubular member 231 and coaxially disposed within the cylindrical expansion member 246 provides greatly improved pushability and axial column strength for causing elongation of the cylindrical expansion member 246 while providing the desired flexibility so that tortuous curves can be negotiated during deployment of the mechanical dilatation and irradiation device 221. The portion 231*c* of the flexible elongate tubular member 231, and particularly within the cylindrical expansion member 246, has a relatively small diameter so that it does not adversely affect the stenosis crossing profile for the mechanical dilatation and irradiation device 221. The use of the inner or safety ribbon 241 prevents undue elongation and unwinding of the coil spring 236 forming a part of portion 231*c* of the flexible elongate tubular member 231 when the cylindrical expansion member 246 is lengthened or elongated. The pull or safety ribbon 241 also limits elongation of the cylindrical expansion member 246 and thereby prevents the elements 251 from being broken off or pulled away from the solder joints 253.

The proximal extremity 223 of the outer flexible elongate tubular member 222 of the mechanical dilatation and irradiation device 221 is provided with control means 261 for causing relative movement between the first or outer flexible elongate tubular member 222 and the second or inner flexible elongate tubular member 231 and can be similar to that hereinbefore described. This control means 261 consists of a fitting 262 which is bonded to the proximal extremity 223 of the outer flexible elongate tubular member 222. The fitting 262 is provided with a male Luer fitting 263 removably mated with a female Luer fitting 264 carried by a Y-adapter 266 which is provided with a central arm 267 and a side arm 268. The side arm 268 is in communication with the lumen 226 of the outer flexible elongate tubular member 222. The inner flexible elongate tubular member 231 extends through the central arm 267 of the y-adapter 266. A rotatable knob 269 is provided on the central arm of the y-adapter 266 for forming a fluid-tight seal between the central arm 267 and the portion 231*a* of the inner flexible elongate tubular member 231. A male Luer fitting 271 is mounted on the proximal extremity of the portion 231*a*. The guide wire 26 extends through the lumen 234 of the inner flexible elongate tubular member 231 and extends beyond the distal extremity thereof.

As hereinbefore described, the control means 261 can include means such as a screw mechanism for causing relative movement between the outer flexible elongate tubular member 222 and the inner flexible elongate tubular member 231.

Operation and use of the mechanical dilatation and irradiation device 221 is substantially similar to that hereinbefore described with respect to the previous embodiments. The mechanical dilatation and irradiation device 221 however has a number of features which may be more advantageous in certain medical procedures. Thus in medical procedures where improved pushability and torquability is required the use of the metal hypotube for the portion 231*b* of the flexible elongate tubular member provides additional pushability and torquability for the catheter facilitating advancement of the mechanical dilatation and irradiation device 221 through more difficult stenoses, particularly where additional torcuability and pushability are desired. This is also true with the distal extremity of the mechanical dilatation and irradiation device 221 in which the inner flexible elongate tubular member 231 has the distal portion 231*c* thereof that includes the compressed coil spring 236 or braided member 238 which extends at least through the expansion member 246 to provide additional pushability for the expansion member 246 while still retaining the desired flexibility. Even though improved pushability is provided, the distal extremity of the mechanical dilatation and irradiation device 221 is still very flexible permitting it to track tortuosities in the vessels being negotiated thereby. Also because of the pushability of the inner flexible elongate tubular member 231, it is possible to obtain maximum extension of the expansion member 246 and thereby a minimum diameter to facilitate crossing of a stenosis with very small openings therethrough with the mechanical dilatation and irradiation device 221. The safety ribbon 241 prevents undue elongation of the inner flexible elongate tubular member 231. In addition, encapsulation of the compressed coil spring 236 or braided member 238 also prevents elongation of the inner flexible elongate tubular member 231.

When the expansion member 246 is being expanded by decreasing the length of the same, such as in the manner shown in FIG. 17, the diameter of the expansion member is increased to its maximum size with great rigidity because of the undulations 256 provided in the elements 251 of the expansion member 246. These undulations 256 aid providing greater radial forces while still retaining the conical or tapered ends with the open interstices to readily permit blood to pass through the expansion member 246 during the time that the expansion member 246 has been expanded to its maximum diameter to apply maximum radial forces to the stenoses which is being dilated during the procedure.

Figures 19, 20, 21, 22, 23, 24, 25:
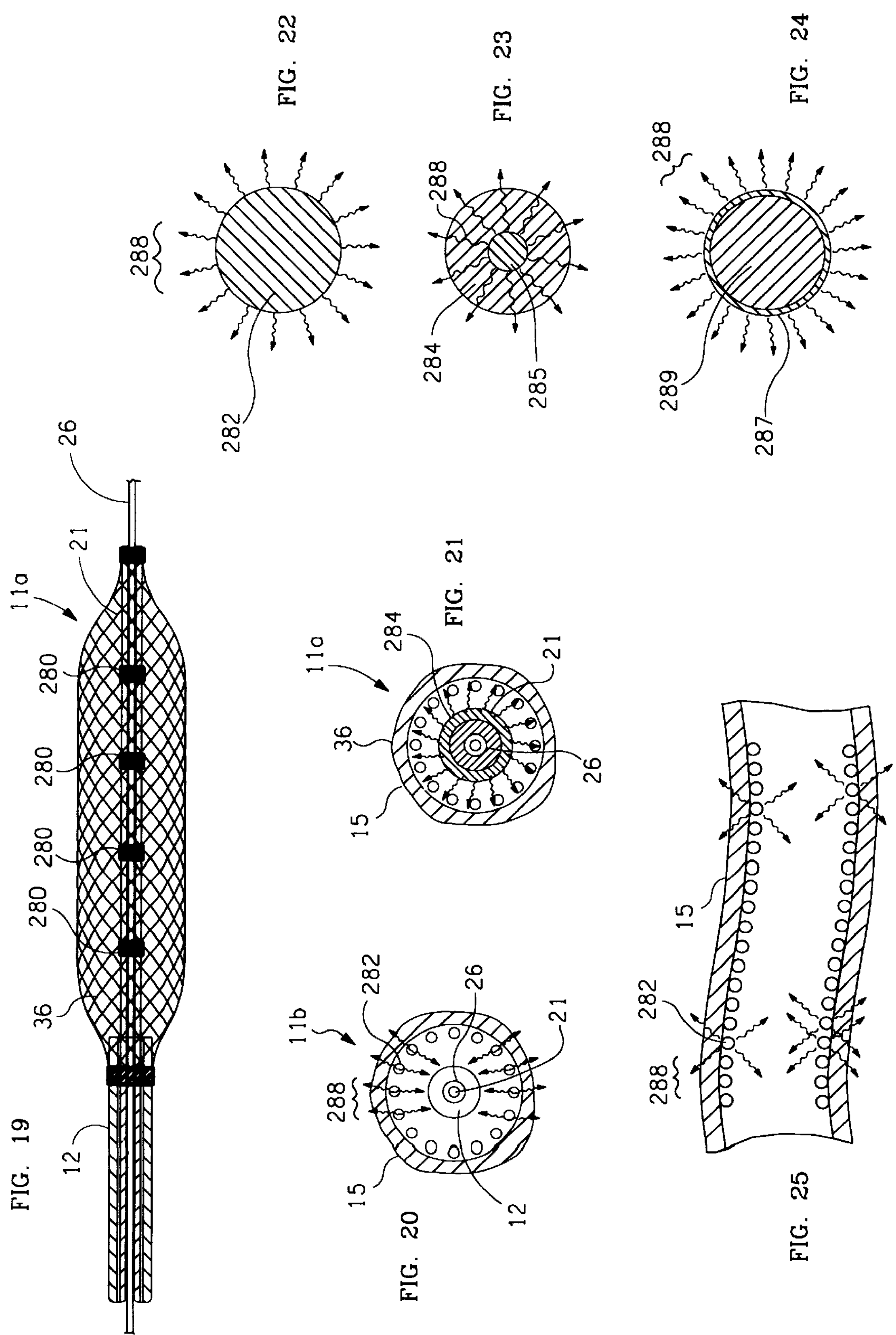
FIG. 19 is a side-elevation view of the expandable mesh with a series of bands on the inner tubular member that are radioactive.
FIG. 20 is a cross sectional view of the radiated flexible elongated elements demonstrating the emission of radiation into the blood vessel.
FIG. 21 is a cross sectional view demonstrating the symmetrical emission of radiation from the inner tubular member located within the expandable mesh.
FIG. 22 is a cross sectional view of the one flexible elongate element (wire) of the expandable mesh demonstrating the symmetrical emission of radiation from the elongate element fabricated with a material which alloys or incorporates the radioisotope within the material.
FIG. 23 is a cross sectional view of the one flexible elongate element (wire) of the expandable mesh demonstrating the symmetrical emission of radiation from a radioactive solid or liquid core within the elongate element.
FIG. 24 is a cross sectional view of the one flexible elongate element (wire) of the expandable mesh demonstrating the symmetrical emission of radiation from a radioactive coating over the elongate element.
FIG. 25 is a cross sectional view of the mechanical dilatation and irradiation device deployed within an arterial segment demonstrating the symmetrical emission of radiation.

FIG. 19 depicts the mechanical dilatation and irradiation device with a series of bands 280 secured to the inner member which is either fabricated from a non-radioactive alloy or coated with a material that becomes radiative by one of the well known activation mechanisms. Any of the standard practices for activating a base material to a radioactive state known by those skilled in the art can be utilized or employed with the present invention. Alternatively, the bands 280 can be alloyed from or coated with a material that is radioactive (undergoing nuclear decay).

The radioisotope used for these purposes (i.e. either incorporating the radioisotope into the material or subsequently activating the material by exposure to radiation source) may be an alpha, beta or gamma emitter or any combination of these. For clinical applications, a radioactive emitter with a half life in the range between 10 hours and 50 days would be ideal. In addition, an ideal characteristic of the emitting radiation is that it does not travel long distances from the source, being absorbed by the tissue that is in close proximity to the radiation source. Furthermore, modest levels of radiation are desirable since significant levels of radiation are well known to damage the non-proliferative cells.

An example of an isotope that could be alloyed into the base material or subsequently activate the radioactive bands 280 is phosphorus 32, a beta emitter with a half-life of approximately 14 day. Another example for an ideal radiation emitter would be vanadium 48 another beta emitter with a half-life of approximately 16 days but also emits a small portion of it total energy as gamma radiation. Other potential radioisotopes are platinum 125 which emits both beta particles and gamma rays with a half life of 4.1 days. An example of a potential gamma ray emitter is iridium 189 with a half life of 12 days.

Alternatively, the entire inner member of the expandable mesh can be a radioactive source by utilizing either of the means described above. FIG. 21 is a cross-sectional view of FIG. 19 showing either a single radioactive band 284 or the entire inner tubular member as the radiation source. FIG. 21 also demonstrates the uniform path an alpha or beta particle, or gamma ray would project from these sources to the vessel wall 15.

In another embodiment of the present invention, the flexible elongate elements 282 of the present invention can themselves be the radioactive source as shown in FIG. 20. As demonstrated in the cross-sectional view of a flexible elongate element 282 (see FIG. 22), the element can be alloyed with or subsequently activate a non-radioactive material to emit radiation 288 uniformly to the vessel wall. As discussed above for the inner member or the bands which surround the member, the alloyed radioactive material can be represented by a number of isotopes. Also, as discussed above, any of the standard practices for activating a base non-radioacive material to a radioactive state known by those skilled in the art can be utilized or employed with the present invention.

Alternatively, as shown in FIG. 23, the flexible elongate element 284 can have a hollow core 285 that is filled with a solid, liquid or gaseous material that either is radioactive or with a non-radiactive solid, liquid or gaseous material that can subsequently become radioactive by standard activation mechanisms. The radioactive elongate element will emit radiation 288 uniformly to the vessel wall 15 as demonstrated in FIG. 23.

A further alternate is shown in FIG. 24 where the flexible elongate element is coated with a non-radioactive material that becomes radioactive by one of the well known activation mechanisms yielding a radioactive elongate element 289. Alternatively, a coating comprising a radioactive material 287 can be applied to the flexible elongate element rendering the present invention radioactive. The uniform distribution of radioactive alpha or beta particles or gamma rays 288 is demonstrated in cross-section in FIGS. 20 and 25.

An additional embodiment not shown but contemplated by the applicant is to utilize the present invention with a radioactive guidewire that can be inserted through the internal lumen 26 of the over-the-wire design or through the distal lumen 107 of the rapid exchange design to irradiate an obstruction while and subsequent to the dilatation procedure. The advantages of using the present invention include exposing a vascular segment or obstruction to an intravascular radiation source for prolonged periods while allowing continuous perfusion of blood into the distal to the treatment area. Furthermore the embodiment is capable of providing a uniform dose of radiation to the vascular segment by centering the radioactive guidewire in the vessel lumen.

From the foregoing, it can be seen that there has been provided a mechanical dilatation and irradiation device which can be used in the same manner as a balloon catheter in dilating a vessel segment or deploying a stent during an interventional procedure with the outstanding advantage that blood can continue to flow to the distal blood vessel during the procedure. This permits a longer vessel dilatation and irradiation without tissue ischemia. In addition, perfusion of side branches continues through the flexible cylindrical member. Furthermore, the dilatation and irradiation device provides delivery of a uniform dose to the affected vessel walls via either radiation delivered from the radioactive expansion member or from the radioactive flexible elongate elements centered within the vessel while the distal mesh is in its expanded state. Furthermore, the mechanical dilatation and irradiation device also provides the advantages of known expanded non-compliant diameter and therefore exact sizing. In addition, there is no possibility of a balloon rupture with leakage of radioactive materials due to protrusions from the surface of the stent or prosthesis perforating the balloon during deployment.

I claim:

1. A catheter for dilating and irradiating an obstruction within a vascular segment or a body passageway which comprises:

said catheter having a distal end and a proximal end;

a substantially cylindrical shaped expansion member located on said distal end, said expansion member having a first end and a second end, said first end being a distance from said second end;

an altering means engagable to said first end and said second end of said expansion member for altering said distance there between to move said expansion member between a first configuration wherein said expansion member is characterized by a first diameter and a second configuration wherein said expansion member is characterized by a second diameter, said second diameter being greater than said first diameter, wherein said expansion member is adapted to allow blood to flow through said expansion member while said expansion member is in said second configuration; and a radioactive source located at said distal end.

2. The catheter as recited in claim 1 wherein said expansion member comprises a first plurality of flexible elongate elements helically wound in a first direction of rotation and a second plurality of flexible elongate elements helically wound in a second direction of rotation to form a braid.

3. The catheter as recited in claim 2 wherein each flexible elongate element has a circular cross section defined by a diameter and said diameter is in a range of approximately 0.001 to 0.010 inches.

4. The catheter as recited in claim 1 further comprising said radioactive source employing material that emits radiation from a radioisotope.

5. The catheter as recited in claim 4 further comprising said radioisotope is located within a structural material of said expansion member.

6. The catheter as recited in claim 4 further comprising said radioisotope being incorporated into the structural material of said expansion member.

7. The catheter as recited in claim 4 further comprising said radioisotope is fixed to a surface of said expansion member.

8. The catheter as recited in claim 4 further comprising said radioisotope is alloyed into a structural material of at least one band surrounding an inner tubular member on distal end of said catheter.

9. The catheter as recited in claim 4 further comprising said radioisotope is alloyed into the material comprising an inner tubular member of said catheter.

10. The catheter as recited in claim 4 further comprising said radioisotope is alloyed into a structural material used to fabricate at least one flexible elongate element of the expansion member.

11. The catheter as recited in claim 4 further comprising said radioisotope is either a solid, liquid or gaseous material contained within a lumen of at least one flexible elongate element of the expansion member.

12. The catheter as recited in claim 4 further comprising said radioisotope is a coating affixed to at least a portion of the outer surface of at least one flexible elongate element of the expansion member.

13. The catheter as recited in claim 1 further comprising said radioactive source consists of a non-radioactive material that is activated to become radioactive.

14. The catheter as recited in claim 1 further comprising said radioactive source is a beta particle emitting radioisotope.

15. The catheter as recited in claim 1 further comprising said radioactive source is a gamma emitting radioisotope.

16. The catheter as recited in claim 1 further comprising said radioactive source is an alpha emitting radioisotope.

17. The catheter as recited in claim 1 further comprising said radioactive source as having any combination of alpha, beta or gamma emitting radioisotope.

18. The catheter as recited in claim 1 further comprising said radioactive source having a half-life of less than 100 days.

19. The catheter as recited in claim 1 further comprising said radioactive source being substantially centered within a vessel segment to uniformly expose said segment with radiation.

20. A mechanical dilatation and irradiation catheter comprising:

said catheter having a distal end and a proximal end, said catheter having an inner member and an outer member;

an expandable mesh positioned on said distal end adapted to dilate an obstruction in a vessel, said mesh having a first contracted diameter and a second expanded diameter, said second expanded diameter being larger than said first contracted diameter;

said mechanical dilatation and irradiation catheter being adapted to dilate said obstruction and expose said obstruction to radiation;

said expandable mesh adapted to allow blood perfusion while said mesh is in said second expanded diameter; and said mechanical dilatation and irradiation catheter having a radioactive source located at said distal end.

21. The catheter as recited in claim 20 further comprising said radioactive source employing material that emits radiation from a radioisotope.

22. The catheter as recited in claim 21 further comprising said radioisotope is located with the structural material of said expandable mesh.

23. The catheter as recited in claim 21 further comprising said radioisotope is fixed to a surface of said expandable mesh.

24. The catheter as recited in claim 21 further comprising said radioisotope is alloyed into the material of at least one band surrounding said inner member of said catheter.

25. The catheter as recited in claim 21 further comprising said radioisotope is alloyed into the material comprising said inner member of said catheter.

26. The catheter as recited in claim 21 further comprising said radioisotope is alloyed into the material used to fabricate at least one flexible elongate element of the expansion member.

27. The catheter as recited in claim 21 further comprising said radioisotope is either a solid, liquid or gaseous material contained within a lumen in at least one flexible elongate element of the expansion member.

28. The catheter as recited in claim 21 further comprising said radioisotope is a coating affixed to at least a portion of the outer surface of at least one flexible elongate element of the expansion member.

29. The catheter as recited in claim 20 further comprising said radioactive source consists of a non-radioactive material that is activated to become radioactive.

30. The catheter as recited in claim 20 further comprising said radioactive source is a beta particle emitting radioisotope.

31. The catheter as recited in claim 20 further comprising said radioactive source is a gamma emitting radioisotope.

32. The catheter as recited in claim 20 further comprising said radioactive source is an alpha emitting radioisotope.

33. The catheter as recited in claim 20 further comprising said radioactive source as having any combination of alpha, beta, gamma emitting radioisotope.

34. The catheter as recited in claim 20 further comprising said radioactive source having a half-life of less than 100 days.

35. The catheter as recited in claim 20 further comprising said radioactive source being substantially centered within a vessel segment to uniformly expose said segment to radiation.

36. A method for dilating and irradiating an obstruction in a body passageway which comprises the steps of:

exposing an expansion member of a catheter to a radiation activation mechanism such that some portion or all of said expansion member becomes radioactive;

placing said radioactive expansion member within a vessel or body passageway, said expansion member being moveable between a first contracted configuration wherein said member is defined by a first dimension extending in a radial direction of said catheter, and a second expanded configuration wherein said member is defined by a second dimension extending in said radial direction;

advancing said radioactive expansion member to a predetermined site in the vessel or body passageway in said contracted configuration;

applying a force on said radioactive expansion member in an axial direction of said catheter to move said expansion member between said first contracted configuration to said second expanded configuration wherein said expansion member dilates and irradiates an obstruction within said predetermined site while allowing blood to flow through said expansion member.

37. A method as recited in claim 36 which further comprises the step of positioning a guidewire in the body passageway, and wherein said advancing step is accomplished by threading said expansion member over said guidewire.

38. A method as recited in claim 36 which further comprises the step of allowing said expansion member to be in said second expanded configuration for a predetermined period of time to further expose said obstruction to radiation.

39. A method for dilating and irradiating an obstruction in a vessel or body passageway which comprises the steps of:

placing a catheter within a vessel or body passageway, said catheter having an expansion member being moveable between a first contracted configuration wherein said member is defined by a first dimension extending in a radial direction, and a second expanded configuration wherein said member is defined by a second dimension extending in said radial direction, said catheter also containing a radioactive source located at a distal end of said catheter;

advancing said catheter with radioactive source to a predetermined site in the vessel or body passageway in said contracted configuration;

applying a force on said expansion member in an axial direction of said catheter to move said expansion member between said first contracted configuration to said second expanded configuration wherein said obstruction is dilated and irradiated; and allowing blood to flow through said expansion member while said expansion member is in said expanded configuration.

40. A method as recited in claim 39 which further comprises the step of positioning a guidewire in the body passageway, and wherein said advancing step is accomplished by threading said catheter over said guidewire.

41. A method as recited in claim 39 which further comprises the step of allowing said expansion member to be in said second expanded configuration for a predetermined period of time to further expose said obstruction to radiation.

* * * * *